(12) United States Patent
Oooka et al.

(10) Patent No.: US 8,173,802 B2
(45) Date of Patent: May 8, 2012

(54) METHOD FOR PRODUCING PIPERIDIN-4-ONE DERIVATIVE

(75) Inventors: Hirohito Oooka, Takaoka (JP); Yasushi Shibata, Odawara (JP); Hiroki Inoue, Takaoka (JP); Tsutomu Imagawa, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 329 days.

(21) Appl. No.: 12/311,315

(22) PCT Filed: Oct. 10, 2007

(86) PCT No.: PCT/JP2007/069741
§ 371 (c)(1),
(2), (4) Date: Mar. 26, 2009

(87) PCT Pub. No.: WO2008/044701
PCT Pub. Date: Apr. 17, 2008

(65) Prior Publication Data
US 2010/0004455 A1    Jan. 7, 2010

(30) Foreign Application Priority Data

Oct. 11, 2006 (JP) .................................. 2006-277086

(51) Int. Cl.
*C07D 471/08* (2006.01)

(52) U.S. Cl. ....................................... 540/461; 540/520

(58) Field of Classification Search .................. None
See application file for complete search history.

(56) References Cited

OTHER PUBLICATIONS

Jones, Maitland Jr. Organic Chemistry Norton: New York 1997, pp. 838-839.*
Brimble et. al. "Efficient Synthesis of the Azabicyclo[3.3.1]nonane Ring System in the Alkaloid Methyllycaconitine Using Bis(alkoxymethyl)alkylamines as Aminoalkylating Agents in a Double Mannich Reaction" European Journal of Organic Chemistry 2005, 2385-2396.*
Kapnang, H. "Nouvelle Methode De Preparation D'Amines Tertiaires" Tetrahedron Letters, 1983, 24(15), 1597-1600.*
Brocke et al., "Application of a Double Mannich Reaction Using *Bis* (aminol) Ethers in the Synthesis of AE Ring Analogues of Methyl Lycaconitine," *SYNLETT*, 2004, No. 13, pp. 2359-2363.

\* cited by examiner

*Primary Examiner* — David K O Dell
(74) *Attorney, Agent, or Firm* — Foley & Lardner LLP

(57) ABSTRACT

Provided is a method for producing a piperidin-4-one derivative useful as an intermediate for agricultural chemicals or pharmaceutical products. A piperidin-4-one derivative represented by formula (III-a) or formula (III-b) is produced by reacting a cyclic bis(aminol)ether compound represented by formula (I) and an acetone derivative represented by formula (II) in the presence of at least one substance selected from the group consisting of protonic acids, Lewis acids, acid halides and dialkyl sulfuric acids.

2 Claims, No Drawings

METHOD FOR PRODUCING PIPERIDIN-4-ONE DERIVATIVE

TECHNICAL FIELD

The present invention relates to a novel method for producing a piperidin cyclic ketal derivative which is a useful intermediate for agricultural chemicals or pharmaceutical products.

BACKGROUND ART

Among piperidin-4-one derivatives useful as an intermediate for agricultural chemicals or pharmaceutical products, it is known that an isotropane derivative having cross-linked structure is produced, for example, by a method wherein cyclopentanone is cyclized in One Step by using a Double Mannich reaction, as shown by the following formula (Patent Reference 1).

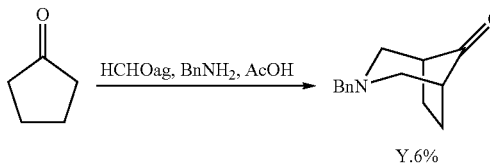

Y.6%

On the other hand, as an improved method of the Double Mannich reaction, a method is known wherein a chain bis(aminol)ether is reacted with a cyclic ketone in the presence of a Lewis acid (see Non-patent Reference 1).

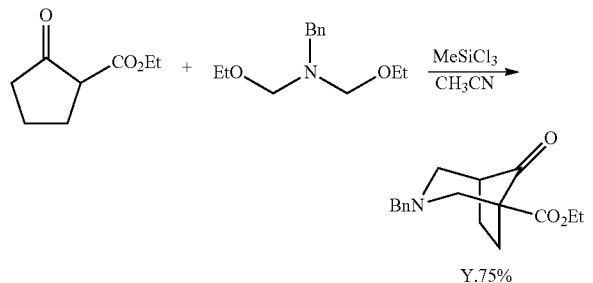

Y.75%

Patent Reference 1: Published Japanese translation of PCT International Publication No. 6-506443
Non-patent Reference 1: Synlett, 2004, (13), 2359-2363

DISCLOSURE OF THE INVENTION

Object to be Solved by the Invention

However, the method described in Patent Reference 1, in spite of its short process duration, had a drawback in that its industrial utility is poor because of the low yield. Further, the method described in Non-patent Reference 1 is poor in industrial utility and lacks versatility in spite of its superior yield, because the method had drawbacks such that it is sometimes hard to be handled as it gives low yield of chain bis(aminol) ethers and thus being unstable; substrates for the Mannich reaction are restricted to only those substrates with a relatively high reactivity; yield of the resultant ester body products is low, since the products are degraded when subjected to hydrolysis or decarboxylation under normal conditions.

The object of the present invention is to provide a method for producing a piperidin-4-one skeleton represented by an isotropane skeleton which has a high yield and a superior working property, and thus can be used industrially.

Means to Solve the Object

The present inventors had made a keen study to solve the above mentioned objects and found out that cyclic bis(aminol)ether compounds can be afforded at a high yield and are stable, and further that the cyclic bis(aminol)ether compounds react in good yield to give piperidin-4-one derivatives with a cheaper reagent than when using chain bis(aminol) ether compounds.

The present invention relates to (1) a method for producing a piperidin-4-one derivative represented by formula (III-a) or formula (III-b),

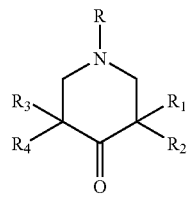

(III-a)

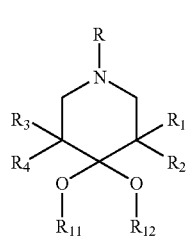

(III-b)

(wherein R represents a hydrogen atom or an organic group, $R_1$-$R_4$ each independently represents a hydrogen atom or an organic group, $R_{11}$ and $R_{12}$ each independently represents a hydrogen atom, hydrocarbon group, acyl group or heterocyclic group, and $R_{11}$ and $R_{12}$ may together form a chemically acceptable ring structure), wherein the method comprises allowing a cyclic bis(aminol)ether compound represented by formula (I)

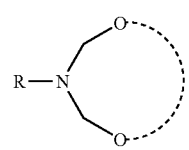

(I)

(wherein R means the same as above, and dotted line represents a functional group which forms a chemically acceptable ring structure) to react with an acetone derivative represented by formula (II)

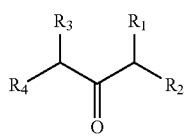

(II)

(wherein $R_1$-$R_4$ means the same as above, and $R_1$ and $R_3$ may together represent a functional group which forms a chemically acceptable ring structure), in the presence of at least one substance selected from the group consisting of a protonic acid, Lewis acid, acid halide and dialkyl sulfuric acid; (2) the method for producing a piperidin-4-one derivative according to (1), wherein the functional group which forms a chemically acceptable ring structure in formula (I) is an alkylene group; (3) the method for producing a piperidin-4-one derivative according to (1) or (2), wherein a compound represented by formula (II) is a cyclic ketone body represented by formula (IV)

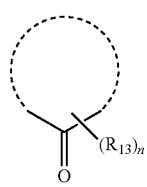

(IV)

(wherein $R_{13}$ represents a hydrogen atom or an organic group, dotted line represents a functional group which forms a chemically acceptable ring structure, n represents 0 or the number of chemically acceptable substituents, and when n is 2 or more, $R_{13}$'s are the same or different, and α-position of a carbonyl group has at least one hydrogen atom); and (4) the method for producing a piperidin-4-one derivative according to any one of (1) to (3), wherein the reaction is conducted in the presence of an alcohol or carboxylic acid.

BEST MODE FOR CARRYING OUT THE INVENTION

Substituents for cyclic bis(aminol)ether compounds represented by formula (I), acetone derivatives represented by formula (II), piperidin-4-one derivatives represented by formula (III-a) or formula (III-b), and cyclic ketone bodies represented by formula (IV) in the present invention are described below.

An "organic group" for the substituents R, $R_1$-$R_4$, and $R_{13}$ may be any group that does not inhibit the reaction of the present invention (e.g., a group which is unreactive under reaction conditions of the present method, or a group which is not a steric barrier to the present reaction), where the examples include a hydrocarbon group and heterocyclic group.

The hydrocarbon group and heterocyclic group also include a hydrocarbon group and heterocyclic group having substituents. The hydrocarbon group includes an aliphatic hydrocarbon group, alicyclic hydrocarbon group, aromatic hydrocarbon group, and a group in which these hydrocarbon groups are bound.

Examples of the aliphatic hydrocarbon group include an alkyl group having about 1 to 20 carbons (preferably 1 to 10, more preferably 1 to 3) such as methyl, ethyl, propyl, isopropyl, butyl, isobutyl, s-butyl, t-butyl, pentyl, hexyl, decyl and dodecyl groups; an alkenyl group having about 2 to 20 carbons (preferably 2 to 10, more preferably 2 or 3) such as vinyl, allyl and 1-butenyl groups; an alkynyl group having about 2 to 20 carbons (preferably 2 to 10, more preferably 2 or 3) such as ethinyl and propynyl groups.

Examples of the alicyclic hydrocarbon group include an cycloalkyl group having about 3 to 20 carbons (preferably 3 to 15, more preferably 5 to 8) such as cyclopropyl, cyclobutyl, cyclopentyl, cyclohexyl and cyclooctyl groups; a cycloalkenyl group having about 3 to 20 carbons (preferably 3 to 15, more preferably 5 to 8) such as cyclopentenyl and cyclohexenyl groups; and a cross-linked cyclic hydrocarbon group such as a perhydronaphthalene-1-yl group, and norbornyl, adamantly and tetracyclo[4.4.0.1$^{2,5}$.1$^{7,10}$]dodecane-3-yl groups.

Examples of the aromatic hydrocarbon group include a group having about 6 to 14 carbons (preferably 6 to 10) such as phenyl, naphthyl and anthranil groups.

Examples of the hydrocarbon group in which an aliphatic hydrocarbon group and an alicyclic hydrocarbon group are bound include a cycloalkyl-alkyl group such as cyclopentylmethyl, cyclohexylmethyl and 2-cyclohexylethyl groups. Further, examples of the hydrocarbon group wherein an aliphatic hydrocarbon group and an aromatic hydrocarbon group are bound include an aralkyl group (e.g., a $C_{7-18}$ aralkyl group such as benzyl and phenethyl), and an alkyl-substituted aryl group (e.g., a phenyl group or a naphthyl group wherein about 1 to 4 $C_{1-4}$ alkyl groups are substituted, such as 4-methylphenyl and 2-ethylnaphthyl).

The hydrocarbon groups described above may have various substituents. Examples of such substituents include hydrocarbon groups enumerated above, as well as a halogen atom (e.g., fluorine atom, chlorine atom, bromine atom and iodine atom), hydroxyl group, oxo group, substituted oxy group (e.g., alkoxy group, aryloxy group, aralkyloxy group, acyloxy group), substituted oxycarbonyl group (e.g., alkoxycarbonyl group, aryloxycarbonyl group, aralkyloxycarbonyl group), acyl group, formyl group, acetal group, ketal group, substituted or unsubstitued carbamoyl group, substituted or unsubstitued carbazoyl group, substituted or unsubstitued amidino group, thioacyl group, substituted or unsubstituted dithiocarbonyl group, substituted or unsubstituted sulfamoyl group, substituted or unsubstituted sulfenyl group, substituted or unsubstituted sulfinyl group, substituted or unsubstituted sulfonyl group, substituted or unsubstituted amino group, nitro group, silyl group, cyano group, heterocyclic group, and a hydroxyl group or carboxyl group that are protected by a common protecting group. Further, an aromatic or non-aromatic hydrocarbon ring or an aromatic or non-aromatic heterocyclic ring may be condensed to the rings of an alicyclic hydrocarbon group or aromatic hydrocarbon ring.

The heterocyclic group includes an aromatic heterocyclic ring and a non-aromatic heterocyclic ring. Examples of the heterocyclic ring include a heterocyclic ring comprising an oxygen atom as a hetero atom (e.g., a 5-membered ring such as furan, tetrahydrofuran, oxazole, isooxazole and γ-butyrolactone rings; a 6-membered ring such as 4-oxo-4H-pyrane, tetrahydropyrane and morpholine rings; a condensed ring such as benzofuran, isobenzofuran, 4-oxo-4H-chromene, chromane and isochromane rings; a cross-linked ring such as 3-oxatricyclo[4.3.1.1$^{4,8}$]undecane-2-one ring and 3-oxatricyclo[4.2.1.0$^{4,8}$]nonane-2-one ring), a heterocyclic ring comprising a sulfur atom as a hetero atom (e.g., 5-membered ring such as thiophene, thiazole, isothiazole and thiadiazole rings; a 6-membered ring such as 4-oxo-4H-thiopyrane ring; and a condensed ring such as benzothiophene ring), and a heterocyclic ring comprising a nitrogen atom as a hetero atom (e.g., a 5-membered ring such as pyrrole, pyrrolidine, pyrazole, imidazole and triazole rings; a 6-membered ring such as pyridine, pyridazine, pyrimidine, pyrazine, piperidine and piperazine rings; a condensed ring such as indole, indoline, quinoline, acridine, naphthyridine, quinazoline and purine rings). These heterocyclic rings may comprise a substituent similar to those substituents that may be comprised in the hydrocarbon groups enumerated above.

With respect to the compounds represented by formulae (I), (II), (III-a), (III-b) and (IV), the "functional group which forms a chemically acceptable ring structure" is exemplified by a divalent hydrocarbon group having 1 to 20 carbons, a hydrocarbon group having 1 to 20 carbons which comprises 1 or more hetero atoms such as N, O and S. A hydrocarbon group herein is exemplified by those monovalent hydrocarbon groups enumerated above for the "organic group" except that the monovalent hydrocarbon group is replaced by a divalent hydrocarbon group. These hydrocarbon groups may comprise a substituent, and the examples of the substituent include those similar to the substituents exemplified above for the "organic group". An alkylene group having 2 to 5 carbons is preferably exemplified.

The dotted line in formula (I) is specifically exemplified by the following functional groups.

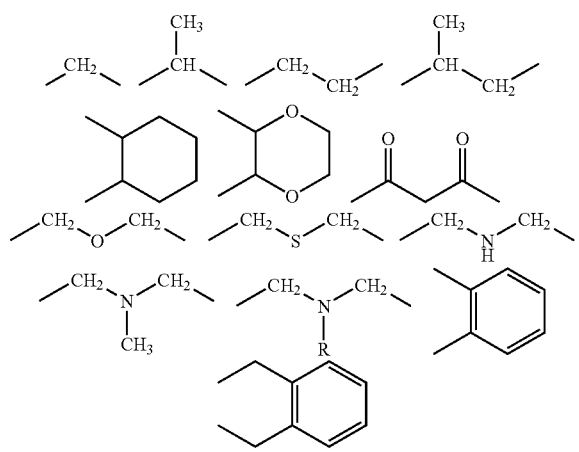

Specific examples of a compound represented by formula (I) include following compounds.

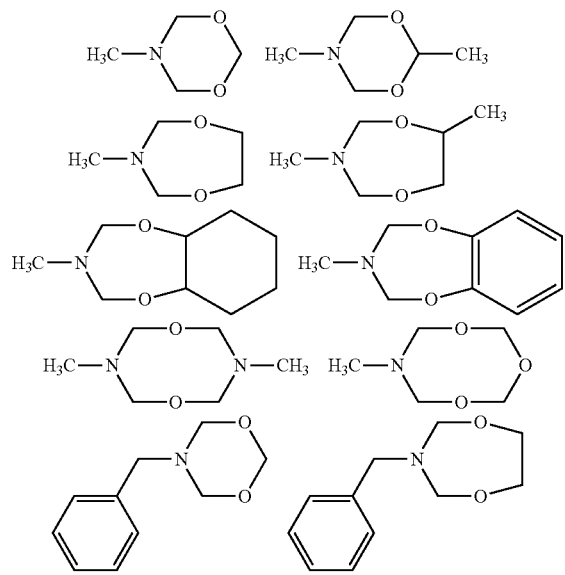

A compound represented by formula (II) can be exemplified by the following compounds. Particularly, a cyclic ketone body is preferably exemplified which is represented by formula (IV) having a structure in which $R_1$ and $R_3$ together form a ring.

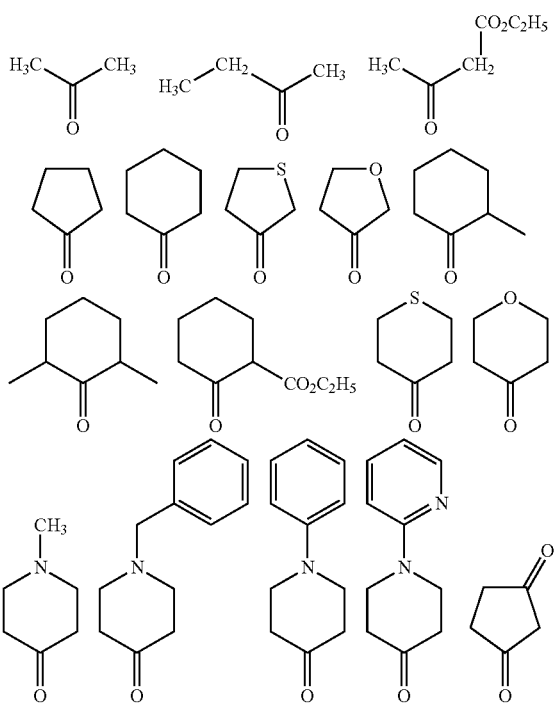

In formula (III-b) obtained by the reaction of the present invention, $R_{11}$ and $R_{12}$ each independently represents a hydrogen atom, hydrocarbon group, acyl group or heterocyclic group, where specific examples thereof include those similar to the appropriate examples among the specific examples for the "organic group". Each atom in such functional group may comprise a substituent within a chemically acceptable range, where the specific examples thereof include those similar to the specific examples for the "organic group". Further, $R_{11}$ and $R_{12}$ may together form a ring structure within a chemically acceptable range, where specific examples thereof include those similar to the specific examples for the dotted line in formula (I).

(Production Method)

In the present invention, the reaction between a cyclic bis(aminol)ether compound represented by formula (I) and an acetone derivative represented by formula (II) is conducted in the presence of at least one substance selected from the group consisting of a protonic acid, Lewis acid, acid halide and dialkyl sulfuric acid.

The ratio of a cyclic bis(aminol)ether compound and an acetone derivative may be appropriately selected by considering such as reactivity and the raw material cost. Usually, the usage amount of bis(aminol)ether compound is 0.1-10 mol, preferably 0.5-2 mol, relative to 1 mol of the acetone derivative.

Examples of the protonic acid for use in the present invention include an inorganic acid such as a hydrochloric acid, hydrogen chloride, sulfuric acid, nitric acid and phosphoric acid; and an organic acid such as formic acid, acetic acid, trifluoroacetic acid, p-toluenesulfonic acid, methanesulfonic acid, and trifluoromethanesulfonic acid. Among these, mineral acids are particularly preferred, where hydrogen chloride and hydrochloric acid are preferably exemplified.

Examples of the Lewis acid for use in the present invention include a metal carbonyl complex such as aluminum(III) bromide, aluminum(III) chloride, gallium(III) chloride, ferric (III) chloride, antimony(V) chloride, tin(IV) chloride, titanium(IV) chloride, zinc(II) chrolide, boron(III) fluoride, boron(III) chloride, copper(II) trifluoromethanesulfonic acid, zinc(II) trifluoromethanesulfonic acid, diphosphorous pentoxide, Mo(CO)$_6$; a complex of a trifluoromethanesulfonic acid lanthanoid series represented by scandium(III) trifluoromethanesulfonic acid; and (R$_{101}$)$_n$SiX$_{4-n}$.

In the formula (R$_{101}$)$_n$SiX$_{4-n}$, R$_{101}$ represents a hydrocarbon group, n represents 1 or 3, where n being 2 or 3 is particularly preferred. When n is 2 or more, R$_{101}$'s may be the same or different. X represents a bromide atom, chloride atom or iodine atom. A hydrocarbon group herein may be any group which does not inhibit the action of a Lewis acid, and includes an aliphatic hydrocarbon group, alicyclic hydrocarbon group, aromatic hydrocarbon group, and a group in which these hydrocarbon groups are bound. The examples thereof include those similar to the exemplifications for the "organic group" above.

Further, when the Lewis acid is (R$_{101}$)$_n$SiX$_{4-n}$ and X is not an iodine atom, either an iodized product of an alkali metal or an iodized product of an alkaline earth metal may further be used together. Examples of the iodized product of an alkali metal or the iodized product of an alkaline earth metal include KI, NaI, RbI, CsI, CaI2 and MgI$_2$, where NaI and KI are preferred.

In the present invention, a highly reactive acid derivative such as an acid halide or dialkyl sulfuric acid may also be used other than those referred to in the above. Examples of these acid derivatives include acetyl chloride, benzoyl chloride, oxalyl chloride, methanesulfonyl chloride, thionyl chloride, thionyl bromide, sulfuryl chloride, sulfuryl bromide, phosphinic chloride, phosphorous trichloride, phosphorous tribromide, phosgene, phosgene derivative, dimethyl sulfate, and diethyl sulfate.

The protonic acid, Lewis acid, acid halide and dialkyl sulfuric acid may each be used alone or may be used in combination of 2 or more kinds thereof. Usage amount of these may be appropriately selected and it is preferred to be in a range of 0.01-5 mol, more preferably 0.1-2.0 mol or 0.1-1 mol, relative to 1 mol of a compound represented by formula (I).

Examples of the solvent for use in the method of the present invention include: water; alcohols such as methanol, ethanol, propanol, isopropanol and butanol; an aliphatic hydrocarbon such as hexane, heptane and octane; an alicyclic hydrocarbon such as cyclohexane; an aromatic hydrocarbon such as benzene, toluene, xylene and ethyl benzene; a halogenated hydrocarbon such as chloroform, dichloromethane and 1,2-dichloroethane; an ether such as diethylether, dimethoxyethane, tetrahydrofuran and dioxane; an amide such as N,N-dimethylformamide and N,N-dimethylacetamide; a nitrile such as acetonitril and benzonitrile; and an ester such as methyl acetate and ethyl acetate. These solvents may be used alone or in combination of 2 or more kinds thereof. It is especially preferred to use alcohols.

Usage amount of the solvent is not particularly limited and may be appropriately selected according to such as types of the reaction system. Usually, an appropriate amount is about 0.5 fold or more in the mass ratio relative to the bis(aminol) ether compound.

In the method of the present invention, compounds represented by formula (III-a) or formula (III-b) can be obtained by selecting reaction conditions.

As a first reaction, a ketone body represented by formula (III-a) is obtained by reacting a compound represented by formula (I) and a compound represented by formula (II).

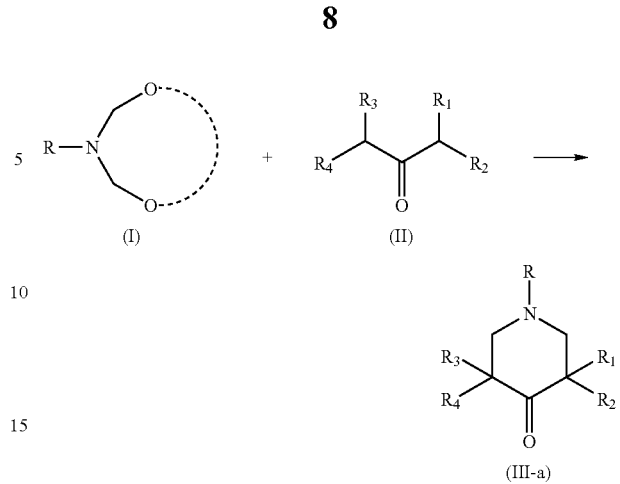

As a second reaction, a compound represented by formula (III-a) is obtained by reacting a compound represented by formula (I) and a compound represented by formula (II). A compound (formula (III-b')) is further obtained which is afforded as a result that diols derived from a compound represented by formula (I) is further reacted with a ketone body represented by formula (III-a) so that a cyclic ketal is formed by the diols in a compound represented by formula (III-b).

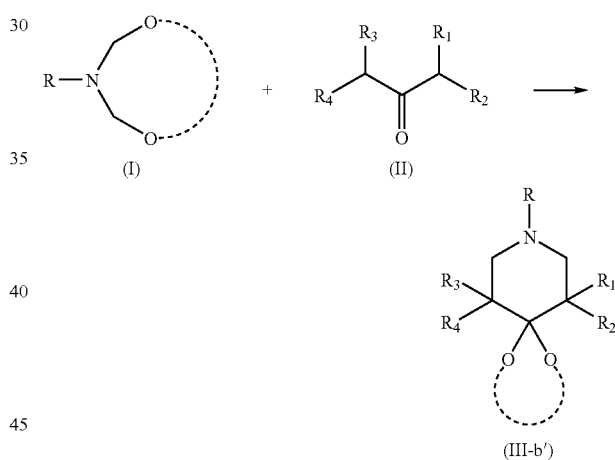

Further, a compound thus obtained which is represented by formula (III-b') can be derivatized to a ketone body represented by formula (III-a) by hydrolyzing the ketal moiety.

As a third reaction, when using an alcohol as a solvent, and/or when a carboxylic acid is used as an acid in the reaction system in the above reaction (the second reaction), a ketone body represented by formula (III-a) reacts with an alcohol and/or carboxylic acid in the system and a compound represented by formula (III-b) is also obtained.

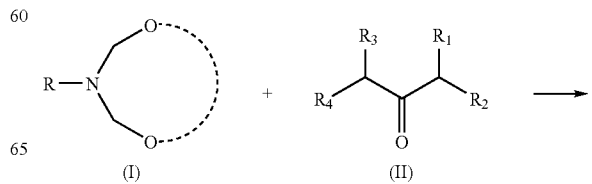

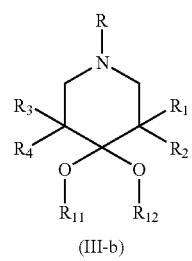

(III-b)

A compound represented by formula (III-b) can be obtained in good yield by allowing an alcohol and/or carboxylic acid to preferentially react to the ketone moiety of a ketone body represented by formula (III-a) than to diols derived from a compound represented by formula (I). The alcohol for use is not particularly limited where the examples include methanol, ethanol, isopropanol, ethyleneglycol and propyleneglycol. Examples of the carboxylic acid for use include a formic acid, acetic acid, propionic acid, oxalic acid and malonic acid.

An alcohol or carboxylic acid for use in the third reaction is not particularly limited, where the specific examples include methanol, ethanol, isopropanol, ethyleneglycol, propyleneglycol, formic acid, acetic acid, propionic acid, oxalic acid and malonic acid. The usage amount of an alcohol or carboxylic acid is not particularly limited, where a range of 2-100 mol relative to 1 mol of a compound represented by formula (I) is preferred, and a range of 2-10 mol or 2-5 mol is more preferred. The alcohol or carboxylic acid may be used alone or may be used as a reaction solvent in combination with other solvent.

Thus obtained compound represented by formula (III-b) can be derivatized to a ketone body represented by formula (III-a) by conducting a hydrolysis on the ketal moiety.

The reaction temperature is not particularly limited and may be appropriately selected according to the types of the reaction constituent or the solvent. Usually, a reaction is conducted at from −50° C. to the boiling temperature of the reaction constituent or the solvent, preferably at 0 to 50° C. The reaction time is also not particularly limited, where reaction is usually conducted for 5 min to 10 hours, preferably for 30 min to 3 hours. The reaction may be conducted at normal pressure or under increased pressure. The reaction atmosphere is not particularly limited as long as the reaction is not inhibited, which, for example, may be any one of such as air atmosphere, nitrogen atmosphere and argon atmosphere. Further, a reaction may be conducted by any method such as a batch reaction, semi-batch reaction and sequential reaction.

After completion of the reaction, the reaction products can be separated and purified by a separation means such as filtration, concentration, distillation, extraction, crystallization, recrystallization, column chromatography, or a separation means consisting of a combination of these means.

The present invention is explained in more detail in the following examples, but the present invention is not limited to these examples.

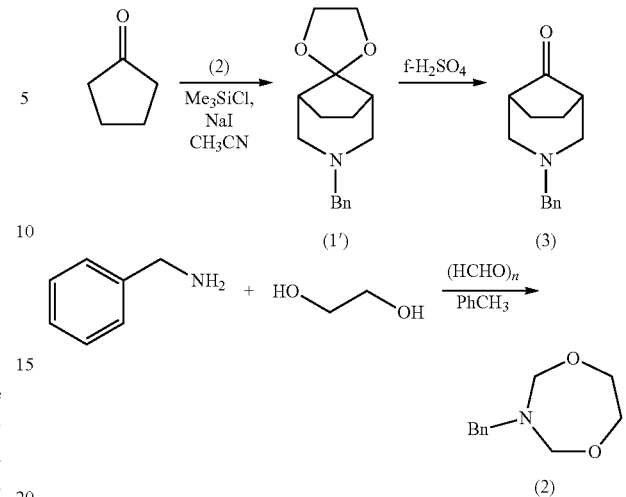

EXAMPLE 1

Synthesis of a 3-Benzyl-3-aza-bicyclo[3.2.1]octan-8-one ethylene ketal compound (1')

1.50 g (10 mmol) of sodium iodide was added to acetonitrile (5 ml) and dissolved under nitrogen atmosphere. 1.09 g (10 mmol) of chlorotrimethylsilane was added dropwise thereto, stirred for 20 min, cooled to 0° C., and 0.42 g (5 mmol) of cyclopentanone was added and stirred for 20 min. Thereto, an acetonitrile (3 ml) solution of 0.97 g (5 mmol) of 3-Benzyl-[1,5,3]dioxazepane(2) was added dropwise for 10 min at the same temperature, which resultant was then restored to room temperature and stirred for 2.5 h. The reaction solution was poured into a saturated sodium bicarbonate water, which was then extracted with ethyl acetate. The organic layer was washed with a saturated saline, dried with magnesium sulfate, filtered and concentrated to obtain compound (1') as a crude purification product, which was further separated and purified using a silica gel column chromatography (hexane/ethyl acetate) to obtain 1.01 g of the target compound (1') (78% yield).

REFERENCE EXAMPLE 1

Acid hydrolysis of compound (1')

0.26 g (1 mmol) of compound (1') purified on a silica gel column was dissolved in 1,4-dioxane (1 ml), to which 30% fuming sulfuric acid (0.3 ml) was added dropwise and stirred for 30 min. The reaction solution was poured into an ice-cold water, which was then neutralized with 1M aqueous sodium hydroxide and extracted with hexane/ethyl acetate. The organic layer was washed with a saturated saline, dried with magnesium sulfate, filtered and concentrated to obtain 3-Benzyl-3-aza-bicyclo[3.2.1]octan-8-one compound (3) as a crude purification product. A HPLC analysis revealed that the yield was 96.0%.

REFERENCE EXAMPLE 2

Synthesis of compound (2)

30.0 g (1 mol) of paraformaldehyde, 31.0 g (1 mol) of ethyleneglycol, and 53.6 g (0.5 mol) of benzylamine were added to a toluene solution (200 ml), and the resultant was heated to undergo an azeotropic dehydration. The reaction was stopped when almost 18 g (1 mol) of water was distilled away and 89.2 g of compound (2) (purity content: ~92%) was obtained as a crude purification product.

EXAMPLE 2

Synthesis of compound (1')

0.83 g (5.5 mmol) of sodium iodide was added and dissolved in acetonitrile (5 ml) under nitrogen atmosphere. Thereto, 0.71 g (5.5 mmol) of dichlorodimethylsilane was added dropwise, stirred for 20 min, cooled to 0° C., added with 0.42 g (5 mmol) of cyclopentanone, and stirred for 20 min. To the resultant, an acetonitrile solution (3 ml) of 0.97 g (5 mmol) of 3-Benzyl-[1,5,3]dioxazepane(2) was added dropwise at the same temperature for 10 min, which resultant was then restored to room temperature and stirred for 1 hour. The reaction solution was poured into a saturated sodium bicarbonate water and extracted with ethyl acetate. The organic layer was washed with a saturated saline, dried with magnesium sulfate, filtered and concentrated to obtain compound (1') as a crude purification product. A HPLC analysis revealed that the yield was 83.4%.

EXAMPLE 3

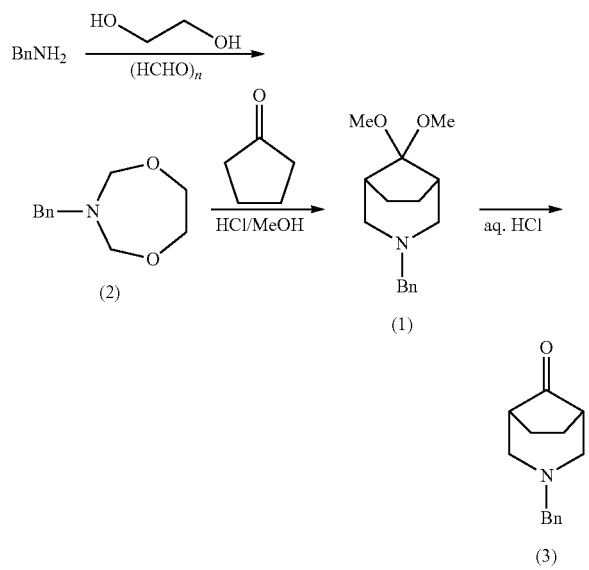

Synthesis of Compound (3)

20.6 g (0.63 mol) of 92% paraformaldehyde, 19.6 g (0.31 mol) of ethyleneglycol, and 32.2 g (0.30 mol) of benzylamine was added sequentially to toluene (60 ml) and subjected to an azeotropic dehydration for 30 min. by heating at reflux temperature to obtain compound (2). Compound (2) was subjected to the next step without being particularly purified.

This compound was diluted with methanol (300 ml), to which 26.5 g (0.32 mol) of cyclopentanone was added, 43.8 g (1.2 mol) of a hydrogen chloride gas was blowed in at 0° C., and stirred for 4 hours at room temperature. Methanol was then distilled away by vacuum concentration, water and toluene were sequentially added thereto, and the toluene layer was preparatively separated by adjusting pH to 12 or higher with 28% caustic soda. The aqueous layer was extracted again with toluene and held together with the toluene layer previously separated. From the obtained toluene layer, 3-Benzyl-3-aza-bicyclo[3.2.1]octan-8-one dimethyl ketal compound (1) was extracted with 6N hydrochloric acid (300 ml) into the aqueous layer as a hydrochloride salt. This aqueous solution was hydrolyzed by heating for 1 hour at 100° C.

The reaction solution was adjusted to pH3 with 28% caustic soda and washed with chloroform. Thus obtained aqueous layer was further added with 28% caustic soda to adjust pH to 12 or higher, which was then extracted with toluene. The HPLC quantitative analysis of thus obtained toluene solution (82.8 g) revealed that this solution contains compound (3) by 52.6 wt % and that the throughout yield through 3 steps was 66.1% when employing the benzylamine used as a standard.

EXAMPLE 4

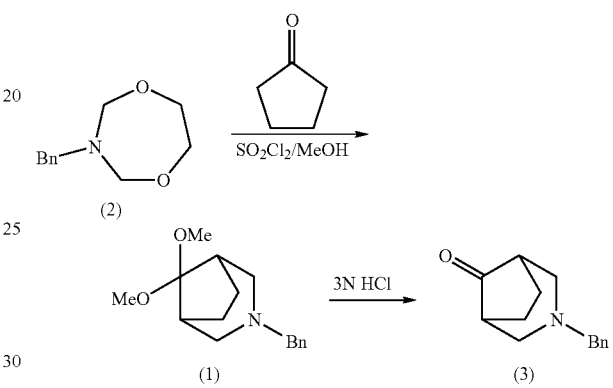

Synthesis of compound (3)

1.35 g (10 mmol) of sulfuryl chloride, 0.84 g (10 mmol) of cyclopentanone, and 0.15 g (0.15 mmol) of a concentrated sulfuric acid were sequentially added to methanol (10 ml) at 0° C., and stirred for 15 min at the same temperature. Thereto, 1.93 g (10 mmol) of compound (2) was added dropwise for 10 min at the same temperature, which resultant was then restored to room temperature and stirred for 4 hours.

To the reaction solution, water (10 ml) was added, followed by addition of 4.28 g (30 mmol) of 28% aqueous sodium hydroxide under ice-cold conditions, and then the resultant was extracted with toluene (20 ml). The organic layer was extracted twice with 3N hydrochloric acid (12.5 ml), then the aqueous solution containing thus obtained compound (1) was refluxed under heat for 2 hours so that it was hydrolyzed to give compound (3). A HPLC analysis revealed that compound (3) was produced as a major product at a purity of 80.3 Area% (thus obtained compound (3) can be used without performing any particular purification).

EXAMPLE 5

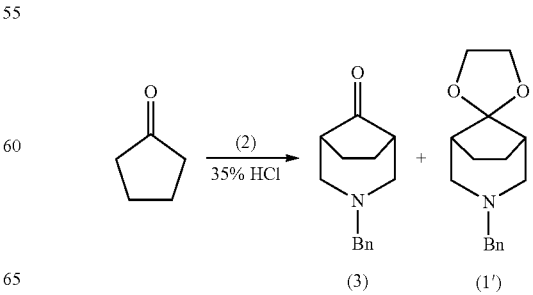

Synthesis of compound (3)

A concentrated hydrochloric acid (10 ml) was slowly added to 0.84 g (10 mmol) of cyclopentanone at 0° C., then 1.93 g (10 mmol) of compound (2) was added dropwise for 5 min at the same temperature. The resultant was restored to room temperature and was left to stand overnight.

A HPLC analysis of the reaction solution confirmed that the compounds (3) and (1') were produced at the phase ratio of 53:47.

EXAMPLE 6

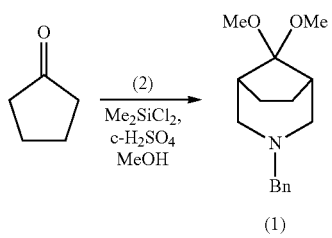

Synthesis of compound (1)

0.84 g (10 mmol) of cyclopentanone was added to methanol (10 ml) and dissolved, which was cooled to 0° C. and 1.29 g (10 mmol) of dichlorodimethylsilane was added dropwise and subsequently 0.15 g (0.15 mmol) of a concentrated sulfuric acid was added, and stirred for 15 min. Thereto, 1.93 g (10 mmol) of compound (2) was added dropwise for 10 min at the same temperature, which resultant was restored to room temperature and stirred for 2 hours.

A 28% aqueous sodium hydroxide solution was added to the reaction solution and extracted twice with toluene. The organic layer was extracted twice with 3N hydrochloric acid, and 28% sodium hydroxide was added to the aqueous layer to adjust the pH to 12 or higher. The aqueous layer was extracted with toluene, and the organic layer was dried with magnesium sulfate, filtered and concentrated to obtain 2.51 g of the target compound (1) as a crude purification product.

EXAMPLE 7

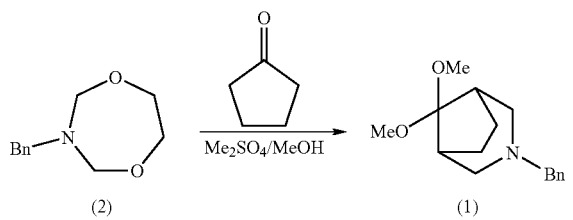

Synthesis of compound (1)

25.2 g (0.1 mol) of dimethyl sulfate was added to methanol (80 ml) at room temperature, then 34.89 g (corresponding to 0.1 mol) of a methanol solution of compound (2), and 9.2 g (0.11 mol) of cyclopentanone were simultaneously added dropwise for 30 min at 40° C.

After this reaction solution had been left stand overnight, a HPLC analysis was conducted and it was confirmed that compound (1) was produced at a production yield of 43 mol %.

EXAMPLE 8

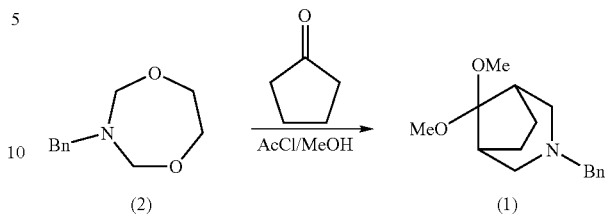

Synthesis of compound (1)

1.93 g (10 mmol) of compound (2) and 0.84 g (10 mmol) of cyclopentanone were added to methanol (10 ml), to which 2.34 g (30 mmol) of acetyl chloride was added dropwise for 10 min at the same temperature and further stirred for 3 hours.

A HPLC analysis of the reaction solution confirmed that compound (1) was produced at a production yield of 64 mol %.

Industrial Applicability

The present invention enabled production of piperidin-4-one derivatives in a good yield at an industrial scale by using a cyclic bis(aminol)ether. A piperidin-4-one derivative produced by the method of the present invention is a useful intermediate for agricultural chemicals or pharmaceutical products as represented by isotropane, and the production method of the present invention is industrially highly useful.

The invention claimed is:
1. A method for producing a piperidin-4-one derivative represented by formula (III-a) or formula (III-b),

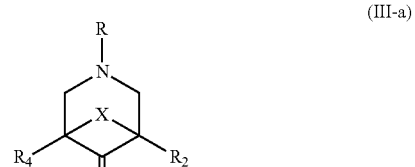

(III-a)

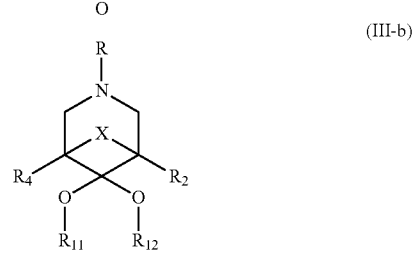

(III-b)

(wherein R represents benzyl group, $R_2$ and $R_4$ each independently represents a hydrogen atom or an organic group, $R_{11}$ and $R_{12}$ each independently represents a hydrogen atom, hydrocarbon group, acyl group or heterocyclic group, and $R_{11}$ and $R_{12}$ may together form ethylene group, and X means an alkylene group having 2 to 5 carbons),
wherein the method comprises allowing ethyleneglycol to react with benzylamine so as to produce 3-benzyl-[1,5,3]dioxazepane, then allowing 3-benzyl-[1,5,3]dioxazepane to react with an acetone derivative represented by formula (II)

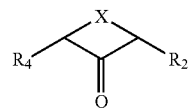
(II)
(wherein $R_2$, $R_4$ and X mean the same as above),
in the presence of at least one substance selected from the group consisting of a protonic acid, Lewis acid, acid halide and dialkyl sulfate.
2. The method for producing a piperidin-4-one derivative according to claim 1, wherein the reaction is conducted in the presence of an alcohol or carboxylic acid.
\* \* \* \* \*